United States Patent
Wang et al.

(10) Patent No.: US 11,826,134 B2
(45) Date of Patent: Nov. 28, 2023

(54) METHOD FOR MEASURING WATER EXCHANGE ACROSS THE BLOOD-BRAIN BARRIER USING MRI

(71) Applicant: UNIVERSITY OF SOUTHERN CALIFORNIA, Los Angeles, CA (US)

(72) Inventors: Danny Wang, Los Angeles, CA (US); Xingfeng Shao, Los Angeles, CA (US)

(73) Assignee: UNIVERSITY OF SOUTHERN CALIFORNIA, Los Angeles, CA (US)

(*) Notice: Subject to any disclaimer, the term of this patent is extended or adjusted under 35 U.S.C. 154(b) by 444 days.

(21) Appl. No.: 16/899,320

(22) Filed: Jun. 11, 2020

(65) Prior Publication Data

US 2020/0390361 A1    Dec. 17, 2020

Related U.S. Application Data

(60) Provisional application No. 62/945,658, filed on Dec. 9, 2019, provisional application No. 62/860,998, filed on Jun. 13, 2019.

(51) Int. Cl.
*A61B 5/055* (2006.01)
*A61B 5/00* (2006.01)
(Continued)

(52) U.S. Cl.
CPC ............ *A61B 5/055* (2013.01); *A61B 5/4064* (2013.01); *G01R 33/5607* (2013.01);
(Continued)

(58) Field of Classification Search
CPC .... A61B 5/4064; A61B 5/055; G01R 33/5618
See application file for complete search history.

(56) References Cited

U.S. PATENT DOCUMENTS

2009/0212773 A1* 8/2009 Feinberg .......... G01R 33/56366
  324/309
2010/0274117 A1* 10/2010 Gunther .......... G01R 33/56366
  600/410
(Continued)

FOREIGN PATENT DOCUMENTS

JP          4319035 B2 *  8/2009  ....... G01R 33/56518

OTHER PUBLICATIONS

D. C. Alsop, "Phase Insensitive Preparation of Single-Shot RARE: Application to Diffusion Imaging in Humans", Magnetic Resonance in Medicine, vol. 38, No. 4, pp. 527-533, Oct. 1997 (Year: 1997).*
(Continued)

*Primary Examiner* — Joel Lamprecht
*Assistant Examiner* — Nyrobi Celestine
(74) *Attorney, Agent, or Firm* — Snell & Wilmer LLP

(57) ABSTRACT

A method for measuring water exchange across the blood-brain barrier includes acquiring diffusion weighted (DW) arterial spin labeling (ASL) magnetic resonance imaging (MRI) signals. The method further includes determining optimal parameters to separate labeled water in capillary and brain tissue compartments. The method further includes estimating water exchange rate across the blood-brain barrier based on the DW ASL MRI signals and the optimal parameters, using a total generalized variation (TGV) regularized single-pass approximation (SPA) modeling algorithm.

18 Claims, 14 Drawing Sheets

(51) Int. Cl.
*G01R 33/563* (2006.01)
*G01R 33/561* (2006.01)
*G01R 33/565* (2006.01)
*G01R 33/56* (2006.01)

(52) U.S. Cl.
CPC ... *G01R 33/5618* (2013.01); *G01R 33/56333* (2013.01); *G01R 33/56341* (2013.01); *G01R 33/56366* (2013.01); *G01R 33/56518* (2013.01)

(56) References Cited

U.S. PATENT DOCUMENTS

| 2014/0210471 A1* | 7/2014 | Stemmer | G01R 33/4835 324/309 |
| 2014/0266195 A1* | 9/2014 | Levin | G01R 33/56509 324/309 |
| 2015/0115958 A1* | 4/2015 | Wang | G01R 33/4835 324/309 |

OTHER PUBLICATIONS

J. Wang et al., "Arterial Transit Time Imaging With Flow Encoding Arterial Spin Tagging (FEAST)," Magnetic Resonance in Medicine, vol. 50, pp. 599-607, 2003 (Year: 2003).*
J. Wang et al., "When perfusion meets diffusion: in vivo measurement of water permeability in human brain," Journal of Cerebral Blood Flow & Metabolism, vol. 27, pp. 839-849, Sep. 2006 (Year: 2006).*
JP-4319035-B2 (Year: 2009).*
R. Bammer et al., "New methods in Diffusion Weighted and Diffusion Tensor Imaging," Magnetic Resonance Imaging Clinics of North America, vol. 17, No. 2, pp. 175-204, May 2009 (Year: 2009).*
F. Knoll et al., "Second Order Total Generalized Variation (TGV) for MRI," Magnetic Resonance in Medicine, vol. 65, pp. 480-491, 2011 (Year: 2011).*
K. Lawrence et al., "A Two-Stage Approach for Measuring Vascular Water Exchange and Arterial Transit Time by Diffusion-Weighted Perfusion MRI", Magnetic Resonance in Medicine, vol. 67, pp. 1275-1284, 2012 (Year: 2012).*
S. M. Spann et al., "Spatio-temporal TGV denoising for ASL perfusion imaging," NeuroImage, vol. 157, pp. 81-96, 2017 (Year: 2017 ).*
M. Fernandez-Seara et al, "Continuous Arterial Spin Labeling Perfusion Measurements Using Single Shot 3D GRASE at 3 T", Magnetic Resonance in Medicine, vol. 54, pp. 1241-1247, 2005 (Year: 2005).*
P. Hales et al, "Combined arterial spin labeling and diffusion-weighted imaging for noninvasive estimation of capillary volume fraction and permeability-surface product in the human brain", Journal of Cerebral Blood Flow & Metabolism, vol. 33, pp. 67-75, Sep. 2012 (Year: 2012).*
P. Hales et al, "A Two-Stage Model for In Vivo Assessment of Brain Tumor Perfusion and Abnormal Vascular Structure Using Arterial Spin Labeling", PLoS One, vol. 8, No. 10, pp. 1-10, Oct. 2013 (Year: 2013).*
H. Pandithasekera, "A Non-Contrast Magnetic Resonance Imaging Technique to Assess Blood-Brain Barrier Permeability", Electronic Thesis and Dissertation Repository, pp. 1-92, Jun. 2014 (Year: 2014).*
E. Kilroy et al, "Reliability of Two-Dimensional and Three-Dimensional Pseudo-Continuous Arterial Spin Labeling Perfusion MRI in Elderly Populations: Comparison With 15O-Water Positron Emission Tomography", Journal of Magnetic Resonance Imaging, vol. 39, pp. 931-939, 2014 (Year: 2014).*
M. Johnston et al, "Multi-TI Arterial Spin Labeling MRI with Variable TR and Bolus Duration for Cerebral Blood Flow and Arterial Transit Time Mapping", IEEE Transactions on Medical Imaging, vol. 34, No. 6, pp. 1392-1402, Jun. 2015 (Year: 2015).*
R. Fang et al, "A spatio-temporal low-rank total variation approach for denoising arterial spin labeling MRI data," 2015 IEEE 12th International Symposium on Biomedical Imaging (ISBI), pp. 498-502, 2015 (Year: 2015).*
J. Guo et al, "Comparing Accuracy and Reproducibility of Sequential and Hadamard-Encoded Multidelay Pseudocontinuous Arterial Spin Labeling for Measuring Cerebral Blood Flow and Arterial Transit Time in Healthy Subjects," Journal of Magnetic Resonance Imaging, vol. 47, No. 4, pp. 1119-1132, Aug. 2017 (Year: 2017).*
Z. Lin et al, "Non-contrast MR imaging of blood-brain-barrier permeability to water", Magnetic Resonance in Medicine, vol. 80, pp. 1507-1520, 2018 (Year: 2018).*
X. He et al, "Diffusion Sensitivity of 3D-GRASE in Arterial Spin Labeling Perfusion", Magnetic Resonance in Medicine, vol. 80, pp. 736-747, 2018 (Year: 2018).*
M. Boland et al, "Accelerated 3D-GRASE imaging improves quantitative multiple post labeling delay arterial spin labeling", Magnetic Resonance in Medicine, vol. 80, No. 6, pp. 2475-2484, May 2018 (Year: 2018).*
B. Macintosh et al, "Measuring the effects of remifentanil on cerebral blood flow and arterial arrival time using 3D GRASE MRI with pulsed arterial spin labelling", Journal of Cerebral Blood Flow & Metabolism, nol. 28, pp. 1514-1522, 2008 (Year: 2008).*
S. Martin et al, "3D GRASE pulsed arterial spin labeling at multiple inflow times in patients with long arterial transit times: comparison with dynamic susceptibility-weighted contrast-enhanced MRI at 3 Tesla", Journal of Cerebral Blood Flow & Metabolism, vol. 35, pp. 392-401, 2015 (Year: 2015).*

* cited by examiner

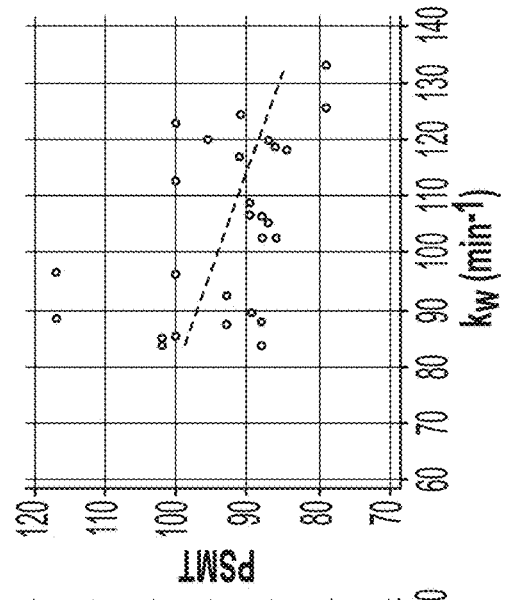
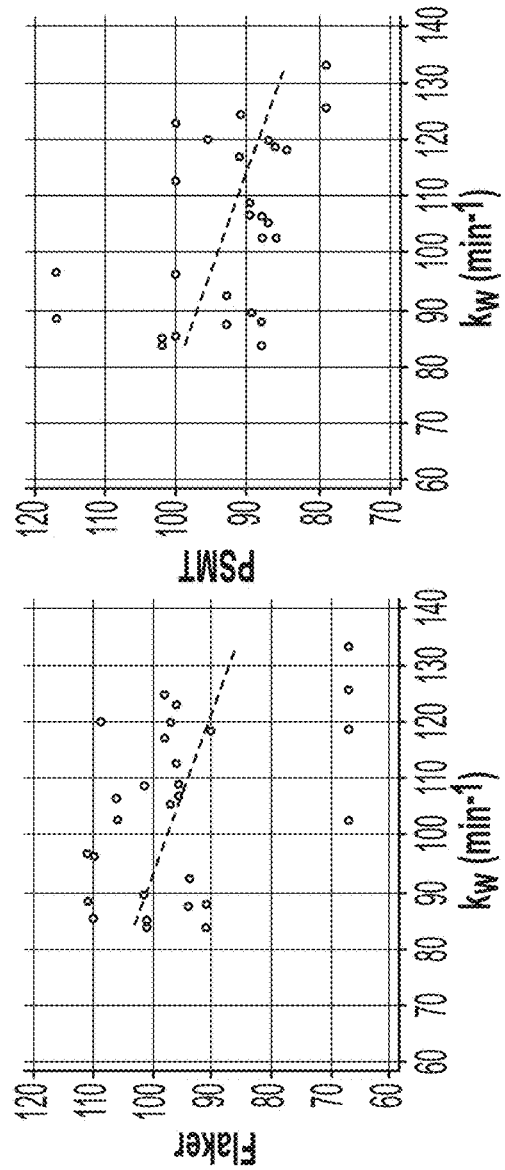
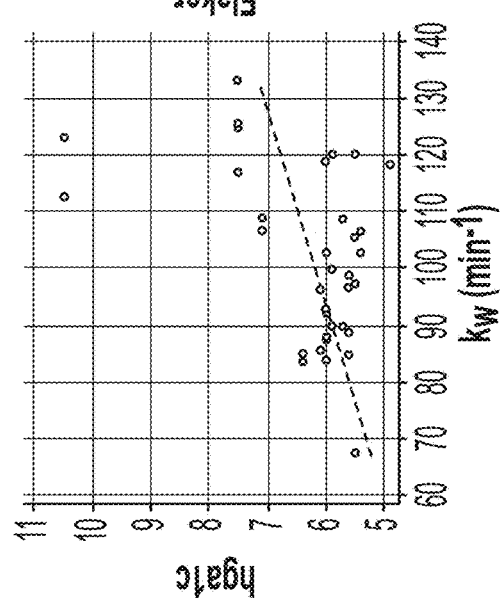
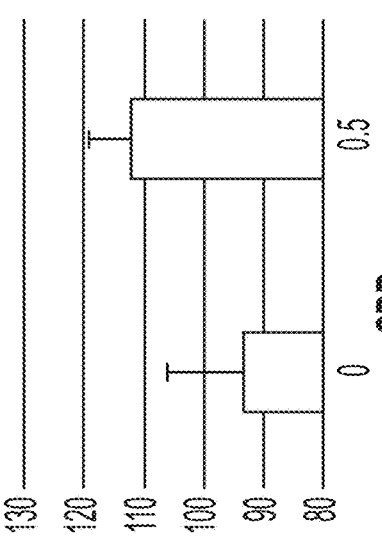
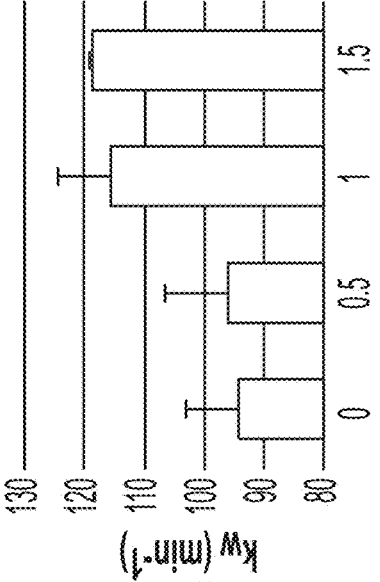
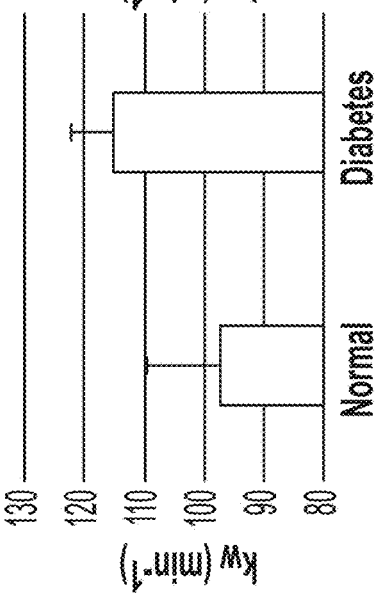

Summary of clinical assessments performed in this study

| Measurement | | Statistics/description |
|---|---|---|
| Medical history | Hypertension | 13 subjects (68.4%) |
| | Daibetes | 6 subjects (31.6%) |
| | Hypercholesterolemia | 14 subjects (73.7%) |
| | Vascular risk factor | Combination of presences of hypertension, diabetes, or hypercholesterolemia (rated from 0 to 3), 3/3/9/4 subjects were rated as 0/1/2/3 |
| Alzheimer's Disease Centers' Uniform Data Set v3 (UDS3) | CDR scale Sum of Boxes (CDR-SB) | Normal (0): 10 subjects (52.6%) |
| | | Questionable cognitive impairment (≥0.5, greater scores indicate more-severe impairment): 9 subjects (47.4%) |
| | Global score (CDR-GS) | Normal (0): 10 subjects (52.6%) |
| | | Questionable cognitive impairment (0.5): 9 subjects (47.4%) |

FIG. 10

| | | |
|---|---|---|
| | Montreal Cognitive Assessment (MoCA) | A measure of visuospatial construction, executive function, verbal memory, attention, working memory, language, and orientation; score≥26 considered as normal (score range; 0-30) |
| NIH toolbox | Flanker | The Flanker is a measure of attention and inhibitory control; *higher* Flanker scores indicate *higher level of ability to attend to relevant stimuli and inhibit attention from irrelevant stimuli*. |
| | Dimensional Change Card Sort Test (DCCS) | The DCCS is a measure of cognitive flexibility; *higher* DCCS scores indicates *higher level of cognitive flexibility*. |
| | Picture Sequence Memory Test (PSMT, version a and b) | The PSMT is a measure of episodic memory, which involves the acquisition, storage and effortful recall of new information; *higher* PSMT score indicate *better episodic memory*. |
| | Pattern Comparison Processing Speed Test (PCPS) | The PCPS is a measure of speed of processing for pattern comparison; *higher* PCPS scores indicate *faster speed of processing*. |
| | Pegboard Dexterity Test (dominant hand) | The test records the time (seconds) required for a participant to place and remove 9 plastic pegs into a plastic pegboard; *faster* completion time indicates *better manual dexterity*. |

FIG. 10 CONT.

| | Grip Strength Test (dominant hand) | The test records the force (pounds) of a participant squeezing a digital hand dynamometer; *greater* force indicates *greater* strength. |
|---|---|---|
| | 4-meter Walking Gait Speed Test | The test records the time (seconds) required for a participant to walk 4 meters at usual pace; *shorter* time indicates *better* gait speed, as a measure of bipedal motion. |
| White matter hyper-intensity (WMH) | Volume | Volume of WMH regions manually measured by clinical fellows from 3D T2 FLAIR images. |
| | Total Fazekes scale | Quantification of WMH lesions, Total Fazekas scale is the sum of 2 scales rated from 0 (absent) to 3 (large confluent areas) in periventricular white matter and deep white matter. 1/1/15/1/1 subjects were rated as 0/1/2/3/4. |

FIG. 10 CONT.

Repeated-measures mixed-effects linear regression coefficients $\beta$

| | | Clinical | | | | | UDS | | | |
|---|---|---|---|---|---|---|---|---|---|---|
| $k_W$ | | Age | Sex (F-0, M-1) | Hyper-tension | Diabetes | Hypercho-lesterolemia | Vascular risk | CDR-SB | CDR-GS | MoCA |
| | Whole brain | 0.49 (0.43) | -10.3 (0.28) | -2.6 (0.78) | 25.7** (<0.001) | 17.8* (0.04) | 9.4* (0.02) | 21.0** (0.001) | 44.6** (0.002) | -0.86 (0.45) |
| | GM | 0.46 (0.43) | -9.2 (0.31) | -2.8 (0.75) | 24.5** (<0.001) | 16.7* (0.05) | 8.8* (0.02) | 20.3** (0.001) | 43.7** (0.002) | -0.79 (0.46) |
| | WM | 0.44 (0.50) | -11.5 (0.26) | -1.8 (0.85) | 26.2** (0.001) | 20.2* (0.03) | 10.3* (0.01) | 22.2* (0.001) | 46.9** (0.003) | -0.95 (0.41) |

| | | NIH toolbox | | | | | | | WMH | |
|---|---|---|---|---|---|---|---|---|---|---|
| $k_W$ | | Flanker | DCCS | PSMTa | PSMTb | PCPS | Dexterity | Strength | WGS | Volumes | Fazekas scale |
| | Whole brain | -0.58 (0.08) | -1.10* (0.02) | -0.98* (0.03) | -1.19** (0.001) | -0.37 (0.28) | 1.59 (0.15) | 0.24 (0.68) | 2.29 (0.70) | 1.68 (0.20) | 10.61* (0.04) |
| | GM | -0.57 (0.07) | -1.09* (0.01) | -0.97* (0.02) | -1.15** (<0.001) | -0.35 (0.28) | 1.51 (0.15) | 8.24 (0.67) | 2.33 (0.68) | 1.72 (0.16) | 10.53* (0.03) |
| | WM | -0.57 (0.12) | -1.09* (0.03) | -0.99* (0.04) | -1.31** (<0.001) | -0.37 (0.31) | 1.52 (0.20) | 0.30 (0.63) | 2.70 (0.69) | 1.75 (0.21) | 11.07* (0.04) |

*P* values are listed in the parenthesises. Significant correlations with *P* values smaller than 0.05 and 0.005 indicated by asterisks in the table.

FIG. 12

METHOD FOR MEASURING WATER EXCHANGE ACROSS THE BLOOD-BRAIN BARRIER USING MRI

CROSS-REFERENCE TO RELATED APPLICATIONS

This application claims the benefit and priority of U.S. Provisional Application No. 62/860,998, entitled "A NOVEL METHOD FOR MEASURING WATER EXCHANGE ACROSS BLOOD-BRAIN BARRIER USING MRI," filed on Jun. 13, 2019, and U.S. Provisional Application No. 62/945,658, entitled "MAPPING WATER EXCHANGE ACROSS THE BLOOD-BRAIN BARRIER USING 3D DIFFUSION-PREPARED ARTERIAL SPIN LABELED PERFUSION MRI," filed on Dec. 9, 2019, the entire disclosure of both being hereby incorporated by reference herein in their entirety.

STATEMENT AS TO FEDERALLY SPONSORED RESEARCH

This invention was made with government support under contract number NS100614 awarded by the National Institute of Health (NIH). The government has certain rights in the invention.

BACKGROUND

1. Field

The present disclosure is directed to systems and methods for measuring water exchange across the blood-brain barriers of humans and animals.

2. Description of the Related Art

The blood-brain barrier (BBB) is formed by endothelial cells (ECs) of cerebral blood vessels with intercellular tight junctions (TJs). The BBB strictly controls the exchanges between blood and brain compartments by limiting passive diffusion of blood-borne solutes while actively transporting nutrients and maintaining water homeostasis in the brain. Accumulating experimental and clinical evidence indicate that BBB dysfunctions (or "opening") are associated with a number of serious central nervous system (CNS) diseases with important social impacts, such as multiple sclerosis (MS), stroke, brain tumors, CNS infection, small vessel disease, and Alzheimer's disease (AD). Existing imaging approaches to assess BBB permeability include positron emission tomography (PET) and magnetic resonance imaging (MRI) by monitoring the (dynamic) uptake of contrast agents in brain tissue. PET has been the primary tool used by the pharmaceutical industry to assess the CNS uptake of radioisotope labeled ligands or candidate drugs with high specificity. Yet the method is expensive and involves undesirable radioactivity. To date, dynamic contrast-enhanced (DCE) MRI using intravenous injection of gadolinium (Gd)-based contrast agents (GBCAs) has been the most widely applied method for imaging BBB permeability in clinical settings. However, GBCAs have potential renal complications and have been linked to Gadolinium deposition in the brain, especially in persons undergoing repeated scans with GBCAs. Both the United States (US) Food and Drug Administration (FDA) and International Society of Magnetic Resonance in Medicine (ISMRM) have recently issued statements to limit the use of GBCAs to clinical circumstances in which the additional information provided by the contrast is necessary in order to reduce the potential for gadolinium accumulation.

Thus, there is a need in the art for systems and methods for safe measurement of permeability of the BBB in humans and animals.

SUMMARY

Disclosed herein is a method for measuring water exchange across the blood-brain barrier. The method includes acquiring diffusion weighted (DW) arterial spin labeling (ASL) magnetic resonance imaging (MRI) signals. The method further includes determining optimal parameters to separate arterial spin labeled water in capillary and brain tissue compartments. The method further includes estimating water exchange rate across the blood-brain barrier based on the DW ASL MRI signals and the optimal parameters.

Also disclosed is a method for measuring water exchange across the blood-brain barrier. The method includes acquiring diffusion weighted (DW) arterial spin labeling (ASL) magnetic resonance imaging (MRI) signals using a diffusion prepared three-dimensional (3D) gradient and spin echo (GRASE) and background suppressed pseudo-continuous arterial spin labeling (pCASL). The method further includes determining optimal parameters to separate arterial spin labeled water in capillary and brain tissue compartments including selecting at least one of optimal b values or optimal diffusion weighting values. The method further includes estimating water exchange rate across the blood-brain barrier based on the DW ASL MRI signals and the optimal parameters.

Also disclosed is a method for measuring water exchange across the blood-brain barrier. The method includes acquiring diffusion weighted (DW) arterial spin labeling (ASL) magnetic resonance imaging (MRI) signals using a diffusion prepared three-dimensional (3D) acquisition techniques including gradient and spin echo (GRASE) and turbo spin echo (TSE), and background suppressed ASL techniques including pseudo-continuous ASL (pCASL), pulsed ASL (PASL), and velocity selective ASL (VS-ASL), and by formulating diffusion gradients in bipolar pairs along at least one of slice direction or other directions and optimizing timing to minimize eddy current. The method further includes determining optimal parameters to separate arterial spin labeled water in capillary and brain tissue compartments including selecting at least one of optimal b values or optimal diffusion weighting values. The method further includes estimating arterial transit time (ATT) and water exchange rate across the blood-brain barrier based on the DW ASL MRI signals and the optimal parameters, using a total generalized variation (TGV) regularized single-pass approximation (SPA) modeling algorithm.

BRIEF DESCRIPTION OF THE DRAWINGS

Other systems, methods, features, and advantages of the present invention will be or will become apparent to one of ordinary skill in the art upon examination of the following figures and detailed description. Additional figures are provided in the accompanying Appendix and described therein.

FIGS. 9A through 9F are plots illustrating hga1c (A), Flanker (B), PSMT (C) versus kw. Linear regression was indicated by the black dashed lines. Bar plot of kw in subject with diabetes and normal subjects (D), and in subject groups with different $CDR_{SOB}$ (E) and $CDR_{global}$ (F) scores according to an embodiment of the present disclosure;

FIG. 10 is a table illustrating a summary of clinical assessments performed in a study using the method of FIG. 2 according to an embodiment of the present disclosure;

FIG. 12 is a table illustrating repeated measures of mixed-effects linear regression coefficients according to an embodiment of the present disclosure.

DETAILED DESCRIPTION

Figure 1:
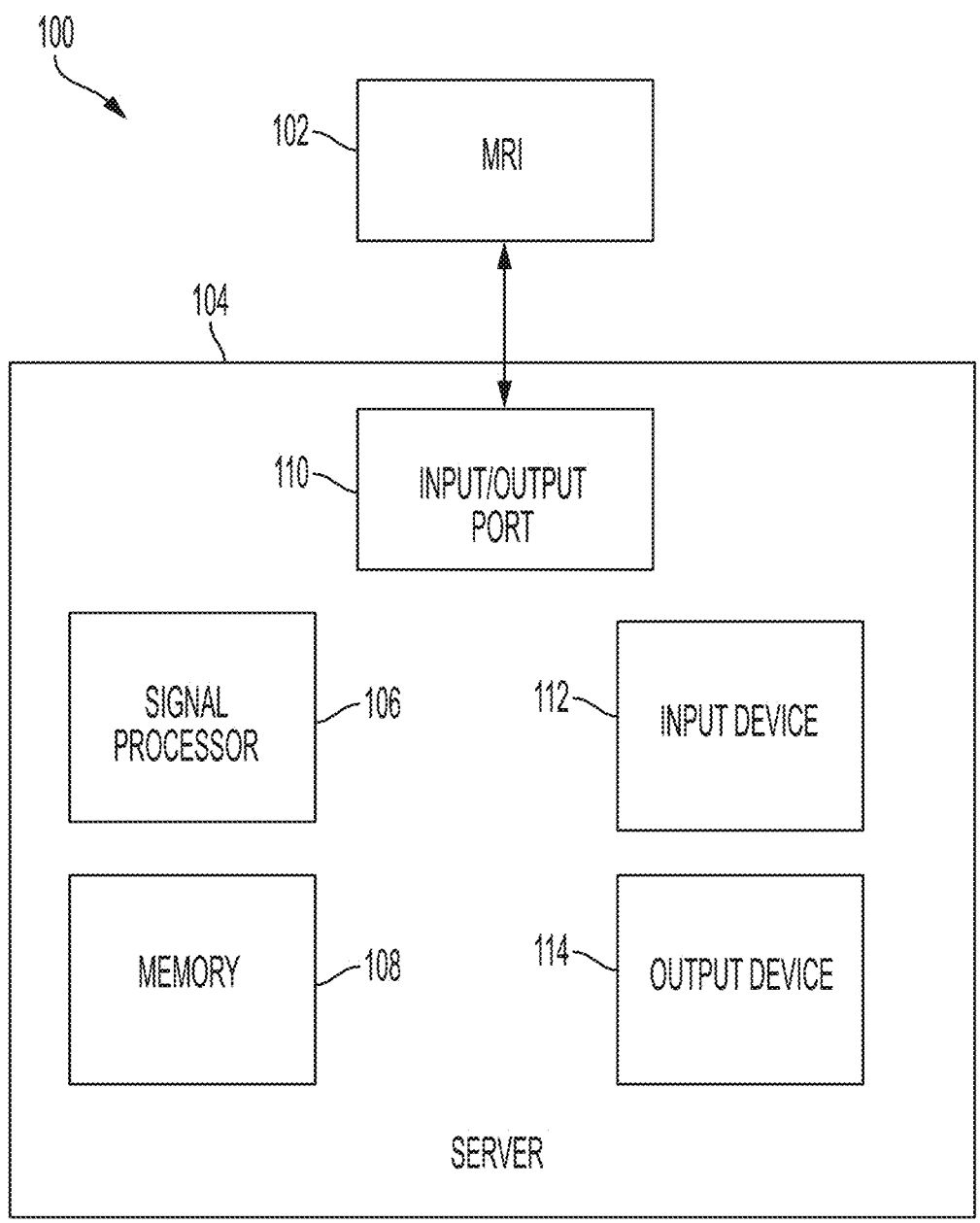
FIG. 1 is a block diagram illustrating a system for measuring water exchange across the blood-brain barrier (BBB) using ASL labeled water according to an embodiment of the present disclosure.

The present disclosure is directed to systems and methods for safely measuring water exchange across the blood-brain barrier (BBB) in humans and animals using diffusion prepared three-dimensional (3D) gradient and spin echo (GRASE) readout and background suppressed pseudo-continuous arterial spin labeling (pCASL). As described in the Background section of this application, existing imaging approaches for measuring the permeability of the BBB include positron emission tomography (PET) and dynamic contrast enhanced (DCE) magnetic resonance imaging (MRI) (which measures the uptake of contrast agents in brain tissue). As further described in the Background section, these methods both present potentially adverse health effects.

An alternative to exogenous contrast agents is water, which is an abundant and endogenous tracer with limited exchange across the BBB. Since gadolinium (Gd)-based contrast agents (GBCAs) have relatively large molecular weights (Gd-DTPA 550 Da), BBB permeability has to reach a critical level before extravasation occurs. Since water molecules have much smaller molecular weight, assessing BBB water exchange could provide a more direct and sensitive biomarker of BBB function at the early stage of disease progression. Arterial spin labeling (ASL) perfusion MRI permits noninvasive measurement of cerebral blood flow using magnetically labeled water as an endogenous tracer. Diffusion-weighted (DW) ASL techniques have been proposed to differentiate the fraction of labeled water in capillary and brain tissue based on their distinctive (~100 fold difference) apparent diffusion coefficients (ADC) (the ADC is typically high in capillaries and low in brain tissue). This DW ASL technique has recently been validated by mannitol administration to open the BBB and using an ischemia-reperfusion model to disrupt BBB in rats. Altered BBB water exchange rate has been detected by DW ASL in subjects with obstructive sleep apnea compared to controls.

Recent evidence suggests that the BBB has limited water exchange. Within the CNS, intercellular tight junctions (TJs) between BBB endothelium cells and the lack of fenestrations in the endothelium itself prohibit water filtration. Most water molecules pass through the BBB by "water channels" consisting of a protein termed aquaporin. With a diameter on the order of a single water molecule, aquaporin only allows for diffusion of 1 molecule at a time. This limited water exchange across the BBB has physiological significance in protecting the brain from edema and swelling. This effect therefore provides the physiological basis for using water exchange rate as a surrogate index of BBB integrity and permeability.

According to the Renkin-Crone equation, the permeability surface product of water ($PS_w$) can be calculated based on the water extraction ratio ($E_w$) and CBF (shown in Equation 1 below):

$$PS_w = -\ln(1-E_w) \times CBF$$

To estimate $E_w$, a long post-labeling delay (PLD) is usually required to allow complete extraction of labeled water into tissue space. Because of longitudinal (T1) relaxation of arterial blood signal, the low SNR of remaining ASL signal makes it impractical to generate reliable voxel-wise water exchange rate maps.

A single-pass approximation (SPA) solution to model ASL signal in the capillary and brain tissue compartments was proposed, while incorporating the exchange rate of water from blood-to-tissue (kw) (shown in Equations 2 and 3 below):

$$\Delta M_c(t) = -\frac{2\varepsilon \cdot CBF \cdot M_0}{\lambda(k_w + R_{1a})} e^{-(R_{1a}-(k_w+R_{1a}))ATT}\left(e^{-(k_w+R_{1a})(t-\delta)} - e^{-(k_w+R_{1a})t}\right) \quad \text{Equation 2}$$

$$\Delta M_b(t) = -\frac{2\varepsilon \cdot CBF \cdot M_0}{\lambda(k_w + R_{1a})} \cdot \frac{k_w}{k_w + (R_{1a} - R_{1b})} \quad \text{Equation 3}$$

$$\left[\frac{e^{-(R_{1a}-R_{1b})ATT}}{R_{1b}}\left(e^{-R_{1b}(t-\delta)} - e^{-R_{1b}t}\right) - \right.$$

-continued $$\frac{e^{-(R_{1a}-(k_w+R_{1a}))ATT}}{(k_w+R_{1a})}\left(e^{-(k_w+R_{1a})(t-\delta)}-e^{-(k_w+R_{1a})t}\right)\Bigg]$$

In Equations 2 and 3, $\Delta M_c(t)$ and $\Delta M_b(t)$ are ASL signals from the capillary and tissue space, respectively; $\varepsilon$ is labeling efficiency, $\delta$ is labeling duration, is the partition coefficient of water in the brain, and $R_{1a}$ and $R_{1b}$ are the longitudinal relaxation rate of arterial blood and brain tissue, respectively. $R_{1a}$ was assumed to be 0.601 s$^{-1}$. The voxel-wise $R_{1b}$ map was fitted from background suppressed (BS) control images acquired at 2 PLDs according to the timing of BS pulses and correspondingly modulated longitudinal signals. The water exchange rate, $k_w$, defined as capillary permeability surface-area product of water (PS$_w$) divided by distribution volume of water tracer in the capillary space (V$_c$), was calculated based on a monotonic relationship with the fraction of capillary signal at a given arterial transit time (ATT), as demonstrated in Equation 4 below:

$$k_w = f(A_1, ATT) \qquad \text{Equation 4}$$

$$A_1 = \frac{\Delta M_c(t)}{\Delta M_c(t)+\Delta M_b(t)}$$

In Equation 4, $f$ was derived from Equations 2 and 3. Capillary signals would be suppressed by a small diffusion gradient because of its pseudo-random motion, and $A_1$ can be calculated by Equation 5 below:

$$A_1 = 1 - \frac{\Delta M_{b_{DW}}}{\Delta M_0} \qquad \text{Equation 5}$$

In Equation 5, $$\Delta M \frac{PLD}{b-\text{value}}$$

is an ASL signal with specific PLD (ms) and b-value (s/mm$^2$) indicated by superscript and subscript, respectively. The appropriate diffusion gradient with a weighting of $b_{DW}$, which suppresses capillary signal while imparting minimal effect on tissue signal, can be determined by biexponential fitting of the DW pCASL signals acquired at multiple b-values. ATT was estimated by the flow-encoding arterial spin tagging (FEAST) method, as a function of the ratio of the vascular suppressed (with diffusion weighting $b_{ATT}=14$ s/mm$^2$, velocity encoding [VENC]=7.5 mm/s) ASL signal to the total sig-nal acquired at a short PLD (900 ms; shown in Equation 6 below):

$$ATT = g\left(\frac{\Delta M_{b_{ATT}}^{900}}{\Delta M_0^{900}}\right) \qquad \text{Equation 6}$$

Estimated $k_w$ is sensitive to noise when tissue fraction is close to 1. A Gaussian filter may be applied to ASL images to improve SNR; however, a predefined threshold of $k_w$ was still required to exclude spuriously high values in local regions. Instead of using a Gaussian filter, the present disclosure proposes a novel total generalized variation (TGV) regularized SPA modeling algorithm for estimating ATT and $k_w$. TGV is an improved mathematical framework based on minimizing both first-order and second-order total variation (TV) for MRI denoising or under-sampled re-construction, which minimizes blotchy (or oil painting like) appearance in MRI images reconstructed with traditional TV algorithm. ATT and $k_w$ can be estimated from DW pCASL data acquired at the PLD of 900 and 1800 ms with respective b-values (shown in Equations 7 and 8 below):

$$\operatorname*{argmin}_{ATT,ATT'}\left[\frac{1}{2\lambda}\cdot\left\|ATT-g\left(\frac{\Delta M_{b_{ATT}}^{900}}{\Delta M_0^{900}}\right)\right\|_2^2 + \right. \qquad \text{Equation 7}$$

$$\left. \alpha_1|\nabla ATT-ATT'|_1 + \frac{\alpha_0}{2}|\nabla ATT'+\nabla ATT'^T|_1\right]$$

$$\operatorname*{argmin}_{k_w,k_w'}\left[\frac{1}{2\lambda}\cdot\left\|k_w-f\left(1-\frac{\Delta M_{b_{DW}}^{1800}}{\Delta M_0^{1800}},ATT\right)\right\|_2^2 + \right. \qquad \text{Equation 8}$$

$$\left. \alpha_1|\nabla k_w-k_w'|_1 + \frac{\alpha_0}{2}|\nabla k_w'+\nabla k_w'^T|_1\right]$$

In Equations 7 and 8, $\lambda=0.05$ is the weighting factor balancing data fidelity and TGV penalty function, $\Lambda$ donates discrete differentiation, $\alpha_1=1$ and $\alpha_0=2$, which were recommended by the field, balances between the first and second derivative of ATT and $k_w$ map.

Referring to FIG. 1, a system 100 for reliable measurement of water exchange across the BBB is shown. The system 100 includes an MRI machine 102 and a server 104. A patient's arterial blood will be non-invasively labeled using ASL technique while the patient is placed in the MRI machine 102.

The server 104 may include a signal processor 106, a memory 108, an input/output port 110, an input device 112, and an output device 114. The signal processor 106 may include any processor, controller, or discrete logic device such as an application-specific integrated controller (ASIC), a field-programmable gate array (FPGA), or the like. The signal processor 106 may be capable of analyzing signals received from the MRI machine 102. The signal processor 106 may further perform various calculations, as described in more detail below with reference to FIG. 2.

The memory 108 may include any non-transitory storage device such as a hard disk drive, a removable memory device, or the like. The memory 108 may store instructions (e.g., computer software) usable by the signal processor 106 to perform logic functions. The memory 108 may further store additional data as requested by the signal processor 106 such as signals received from the MRI machine 102, analyses generated by the signal processor 106, or the like.

The input/output port 110 may include any port capable of at least one of transmitting signals to or receiving signals from the MRI machine 102. For example, as the MRI machine 102 is detecting data from the patient, the detected data may be transmitted to the input/output port 110 of the server 104.

The input device 112 may include any device capable of receiving data from a user or a remote device. For example, the input device 112 may include a network access device (e.g., an ethernet port, a Bluetooth port, a Wi-Fi port, or the like), a mouse, button, keyboard, microphone, or the like. The input device 112 may receive data such as instructions from a user, a program to be executed by the signal processor 106 from a remote device, or the like.

The output device 114 may include any device capable of outputting or transmitting data to a user or a remote device. For example, the output device 114 may include a network access device (e.g., an ethernet port, a Bluetooth port, a Wi-Fi port, or the like), a display, a touchscreen, a speaker, or the like. The output device 114 may output for transmit data such as the result of calculations performed by the signal processor 106, data stored in the memory 108, or the like.

Figure 2:
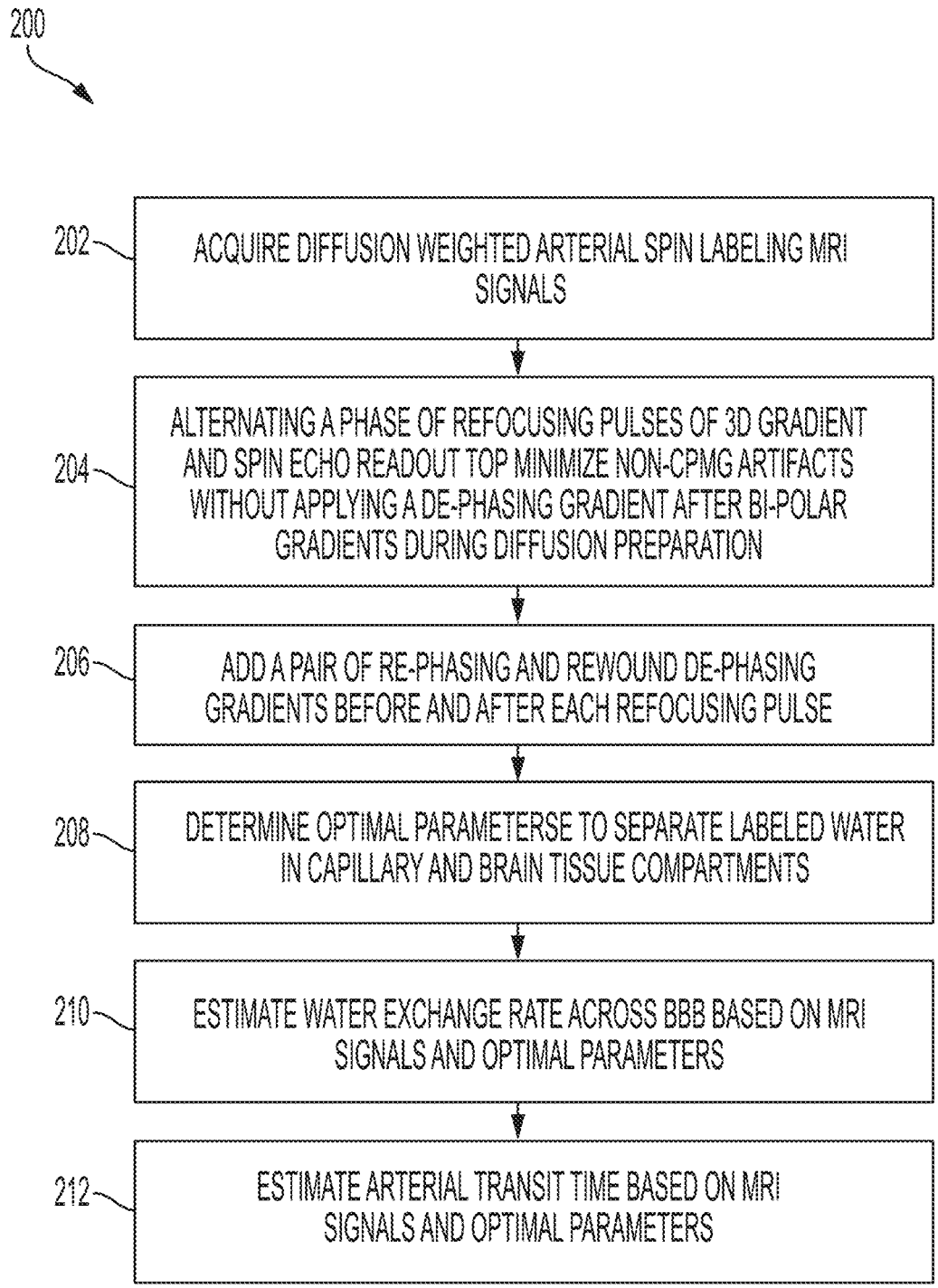
FIG. 2 is a flowchart illustrating a method for measuring water exchange across the BBB using ASL labeled water according to an embodiment of the present disclosure.

Turning now to FIGS. 1 and 2, the system 100 is designed to perform a method, such as a method 200 of FIG. 2, to reliably measure water exchange across the BBB. The method 200 may include three high-level steps: 1) acquire diffusion weighted (DW) ASL signals using a diffusion prepared 3D GRASE pCASL sequence; 2) determine the optimal diffusion weighting (or b values) to separate labeled water in capillary and brain tissue compartments using bi-exponential fitting; and 3) estimate the water exchange rate ($k_w$) across the BBB and arterial transit time (ATT) using a two-step approach and TGV regularized SPA model.

Figure 3:
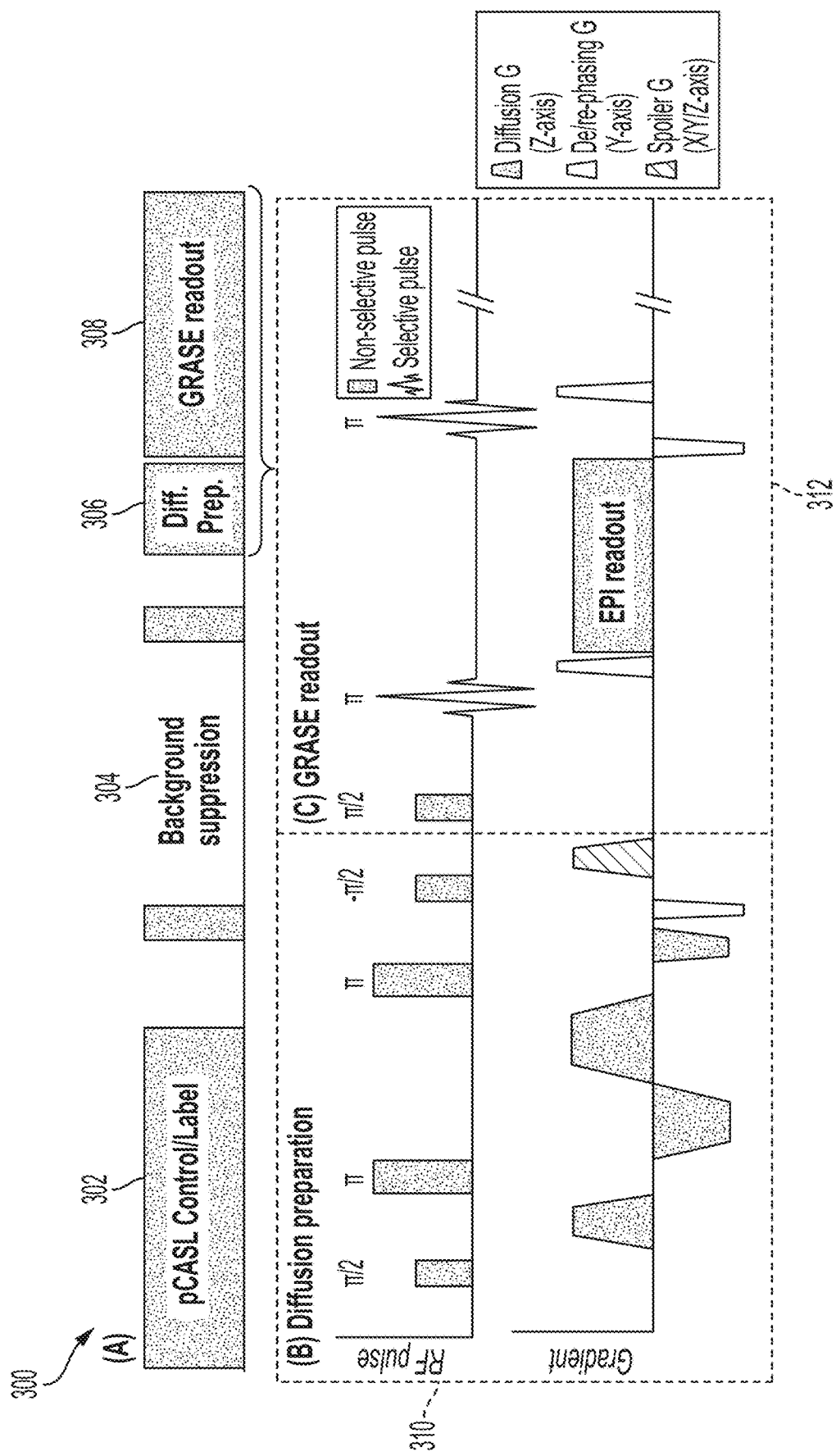
FIG. 3 illustrates a diagram of a diffusion-prepared 3D GRASE pCASL sequence according to an embodiment of the present disclosure.

In particular, the method begins in block 202 where the diffusion weighted arterial spin labeled MRI signals are acquired. FIG. 3 is a diagram of the diffusion-prepared 3D GRASE pCASL sequence, which consists of 4 modules of pCASL labeling 302, background suppression 304, diffusion preparation 306, and GRASE readout 308. Diffusion preparation was implemented before the GRASE readout, as shown in block 310. Diffusion gradients were formulated in bipolar pairs along slice direction and their timing was optimized to minimize the eddy current. Non-selective pulses were used to compensate for effects of field inhomogeneity and two refocusing pulses consisted of MLEV composite pulses to ensure fast and robust refocusing. The transverse signal was tipped-up before readout and spoiler gradients along three axes were added to destroy residual transverse magnetization. In particular, non-selective excitation was used to improve slab profile and re-phasing and rewound de-phasing gradients were added at two sides of EPI readout to maintain MG condition.

Since bulk motion during the diffusion encoding induces spatially varying phase shift $Ø_0$, an additional de-phasing gradient was applied along phase-encoding (PE) direction after the bi-polar gradients to induce a linear phase increment along PE (block 204 of FIG. 2). The purpose of this additional de-phasing gradient was to dephase the non-CPMG signal that is affected by phase errors caused by bulk motion during the diffusion encoding. The magnetization of spins can be described as shown in Equation 9 below:

$$M_x = M_z = M_0 \cos(Ø_0 + Ø) \quad \text{Equation 9}$$

In Equation 9, $M_z$ and $M_x$ are the magnetization at the end of diffusion preparation and right after the excitation pulse for readout, respectively. To satisfy Equation 9, ideal slice profile of 90 degrees (90°) excitation pulse is necessary and a small deviation causes extra signal loss. A non-selective hard pulse was used for GRASE excitation while the imaging slab coverage was determined by the selective refocusing pulses. Ø is the phase induced by the de-phasing gradient, which varies from 0 to $4\pi$ within a single voxel along PE. To compensate for the extra phase, a re-phasing gradient, which is the opposite of the de-phasing gradient, was applied after the first refocusing pulse of GRASE readout. Thus, the magnetization before the first echo ($M_x'$) can be shown in Equation 10 below:

$$M_x' = M_0 \cos(Ø_0 + Ø) \times \exp(-iØ) = \tfrac{1}{2}M_0 \exp(-iØ_0) + \tfrac{1}{2}M_0 \exp(-(Ø_0 + 2iØ)) \quad \text{Equation 10}$$

The average signal within one voxel can be shown by Equation 11 below:

$$\overline{M_x'} = \int_0^{4\pi} \tfrac{1}{2}(M_0 \exp(-iØ_0) + M_0 \exp(-(Ø_0 + 2iØ))) \, dØ = \tfrac{1}{2} M_0 \exp(-iØ_0) \quad \text{Equation 11}$$

The resulting signal is robust to motion, however, at the cost of half signal loss. A pair of re-phasing and rewound de-phasing gradients were added before and after each refocusing pulse to balance the gradient moment (block 206 of FIG. 2), as demonstrated in block 312 of FIG. 3.

In block 208 of FIG. 2, optimal parameters were determined to separate labeled water in capillary and brain tissue compartments. To determine the optimal diffusion weighting or b values, the proposed sequence was performed in four healthy subjects with three post-labeling delays (PLD=1500, 1800 and 2100 ms) and six b-values (b=0, 10, 25, 50, 100, 200 s/mm$^2$). Bi-exponential fitting of DW pCASL signals with six diffusion weightings was conducted to calculate the apparent diffusion coefficients for capillary ($D_c$) and tissue ($D_b$) compartments, and to determine the appropriate $b_{DW}$ which suppress capillary signal with minimal effect on tissue signal (shown in Equation 12 below):

$$\Delta M(b)/\Delta M(0) = A_1 \exp(-b \cdot D_c) + (1-A_1)\exp(-b \cdot D_b) \quad \text{Equation 12}$$

Figure 4:
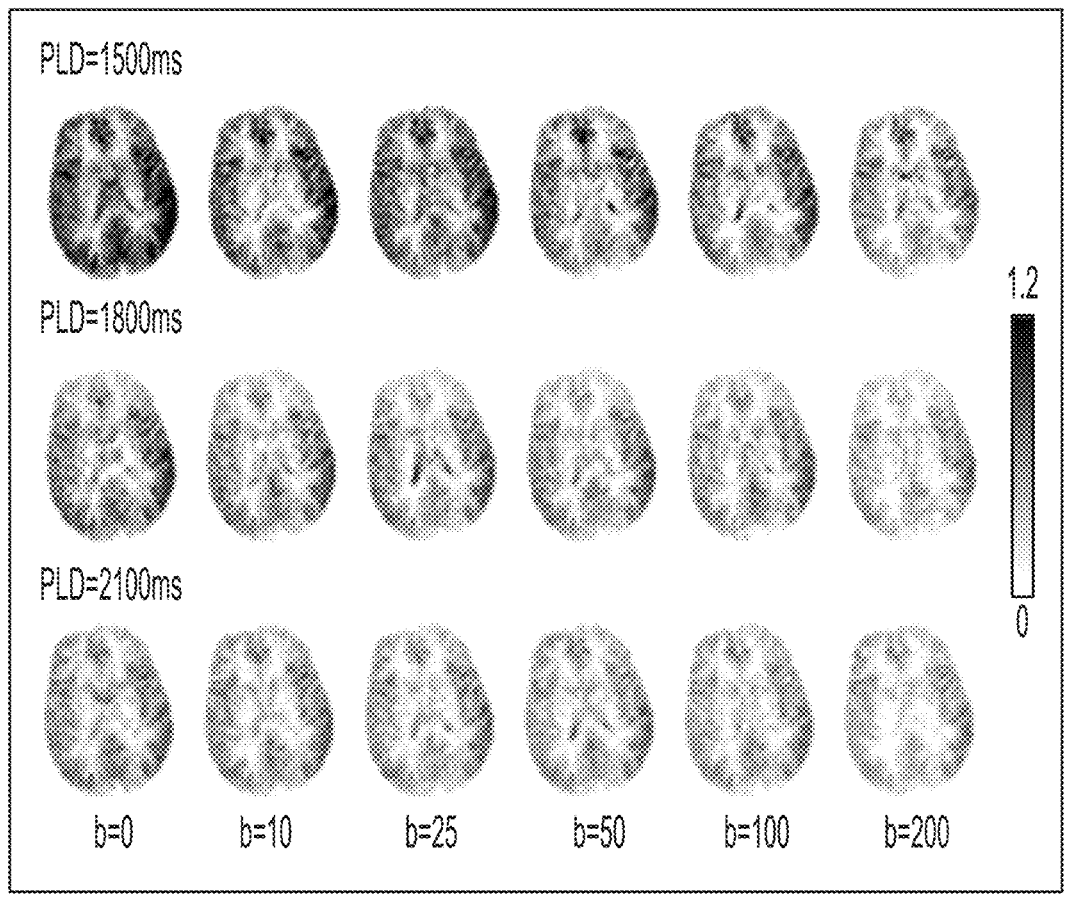
FIG. 4 is a scan illustrating a slice of a DW pCASL image with six diffusion weightings acquired at PLD=1500, 1800, and 2100 milliseconds according to an embodiment of the present disclosure.
Figure 5:
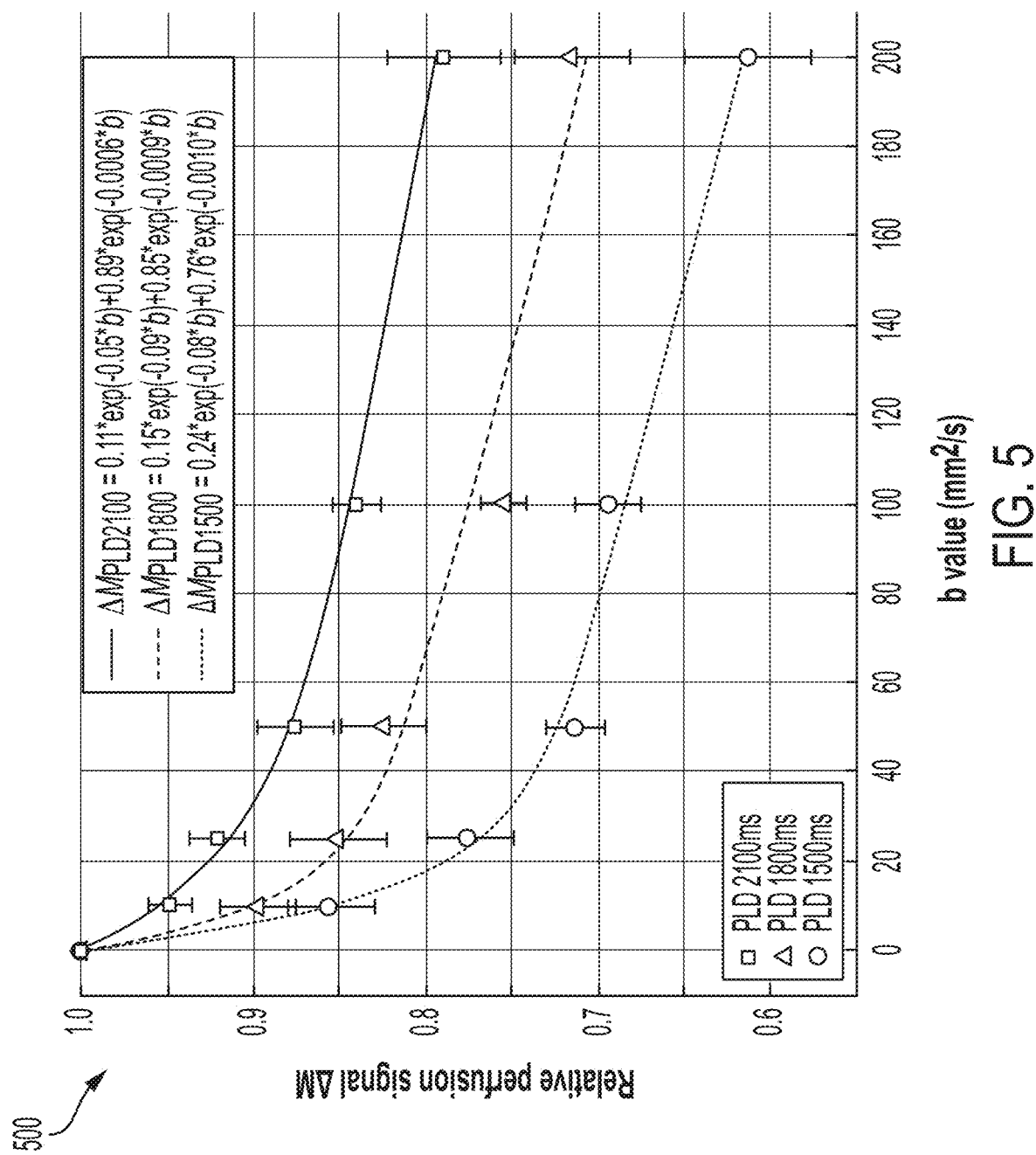
FIG. 5 is a graph illustrating average perfusion signals from four subjects with six diffusion weightings according to an embodiment of the present disclosure.

FIG. 4 illustrates DW pCASL perfusion images of a single slice of a representative subject acquired at 3 PLDs and six b-values. The DW pCASL signal intensity decays with increasing PLD or b-values. Average perfusion signal intensity from four subjects (marks) and bi-exponential fitting results (curves) are shown in a graph 500 of FIG. 5. On average, 76%, 85% and 89% of labeled blood enters brain tissue space when perfusion images are acquired at the PLD of 1500, 1800 and 2100 ms, respectively. Diffusion coefficients of capillary/brain tissue ($D_c/D_b$) were 0.08/0.001 mm$^2$/s, 0.09/0.0009 mm$^2$/s and 0.05/0.0006 mm$^2$/s at PLD 1500 ms, 1800 ms and 2100 ms, respectively. Based on these results, $b_Dw=50$ s/mm$^2$ and PLD=1800 ms were chosen for subsequent $k_w$ measurements, where perfusion signal in capillary and brain tissue compartments were 1.1% and 95.6% of its original signal intensity, respectively. In other words, perfusion signal $\Delta M(b=50, PLD=1800)$ contains 1.1% and 98.9% of capillary and tissue signal, respectively. The differentiation between capillary and tissue space is reliable given the large diffusion coefficient difference (~100-fold) between the 2 compartments. A sensitivity analysis with ±20% change in bDW (50 s/mm2) would induce only ~±1% change in remaining capillary signal.

In block 210 of FIG. 2, the water exchange rate ($k_w$) is estimated across the BBB based on the MRI signals and the optimal parameters. A TGV regularized SPA algorithm has been proposed to model pCASL signal in the capillary and brain tissue compartments while incorporating the exchange rate of water from blood to tissue across the BBB ($k_w$). Water exchange rate $k_w$, defined as capillary permeability surface-area product of water ($PS_w$) divided by distribution volume of water tracer in the capillary space ($V_c$), was calculated based on a monotonically relationship with the fraction of capillary signal at a given arterial transit time (ATT), defined as the duration for the labeled blood to flow from the labeling plane to reach capillaries (shown in Equation 13 below):

$$k_w = f(A_1, ATT), A_1 = \Delta M_c(t)/(\Delta M_c(t) + \Delta M_b(t)) \quad \text{Equation 13}$$

ATT was estimated (block 212 of FIG. 2) by the flow-encoding arterial spin tagging (FEAST) method. Capillary signal would be suppressed by a small diffusion gradient due to its pseudo random motion, and $A_1$ can be calculated by Equation 14 below:

$$A_1 = 1 - \Delta M(b=b_{DW})/\Delta M(b=0) \quad \text{Equation 14}$$

In Equation 14, ΔM is ASL signal. The appropriate diffusion gradient with a weighting of $b_{DW}$, which suppresses capillary signal while imparts minimal effect on tissue signal, can be determined by bi-exponential fitting of the DW pCASL signals acquired at multiple b-values. ATT was calculated from DW pCASL scans acquired at the PLD=900 ms based on the FEAST method with b=0 and 14 s/mm² (VENC=7.5 mm/s). ATT was determined from the ratio of the vascular suppressed ASL signal to the total signal. $k_w$ was calculated from scans acquired at PLD=1800 ms, when the labeled blood reaches the microvascular compartment, with b=0 and $b_{DW}$.

Figure 6:
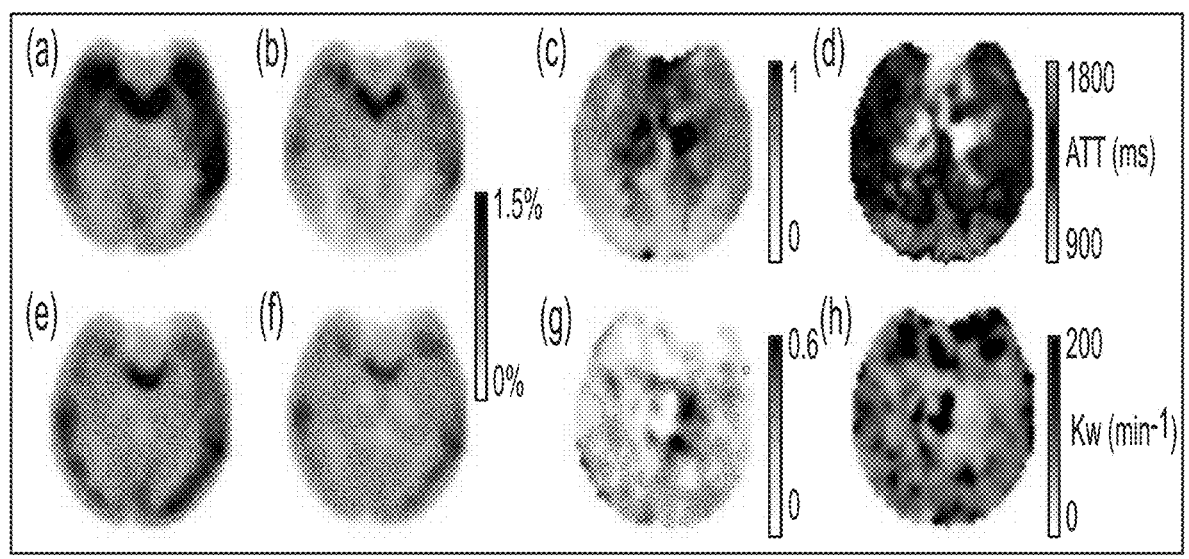
FIG. 6 is a scan illustrating (a) Perfusion signal without diffusion weighting acquired at PLD=900 milliseconds. (b) Perfusion signal with diffusion weighting (b-value)=14 s/mm$^2$ (VEN=7.5 cm/s to suppress vascular signal) acquired at PLD=900 milliseconds. (c) Ratio image: $\Delta M_{PLD900,b14}$ divided by $\Delta M_{PLD900,b0}$. (d) ATT map. (e) Perfusion signal without diffusion weighting acquired at PLD=1800 milliseconds. (b) Perfusion signal with diffusion weighting (b-value)=50 s/mm$^2$ acquired at PLD=1800 milliseconds. (g) Capillary fraction (A1) map. (h) Exchange rate of water (kw) map according to an embodiment of the present disclosure.

FIG. 6 illustrates various steps of the method 200. In particular, (a, b) show a perfusion map acquired at PLD 900 ms without diffusion weighting and with vascular signal suppression (b=14 s/mm²) respectively. (c) shows the ratio map between suppressed vascular signal and total signal. Estimated ATT map is shown in (d). Prolonged ATT is observed in the posterior area, which is consistent with previous findings. (e, f) show perfusion map acquired at the PLD of 1800 ms without diffusion weighting and with the suppression of microvascular/capillary signal (b=50 s/mm²). The calculated capillary fraction $A_1$ and $k_w$ map are shown in (g) and (h), respectively. Smaller $k_w$ indicates reduced water exchange across the BBB with more labeled water remaining in the capillary space.

Figure 7A:
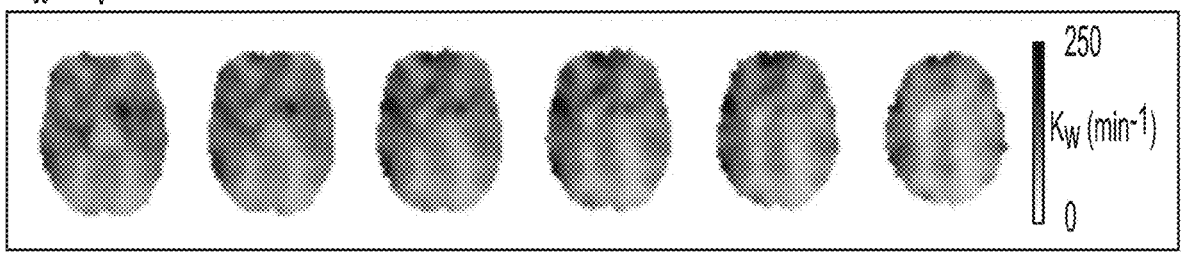
FIGS. 7A and 7B are scans illustrating a water exchange rate ($k_w$) map of six representative slices from test and retest experiments of a single subject according to an embodiment of the present disclosure.
Figure 7B:
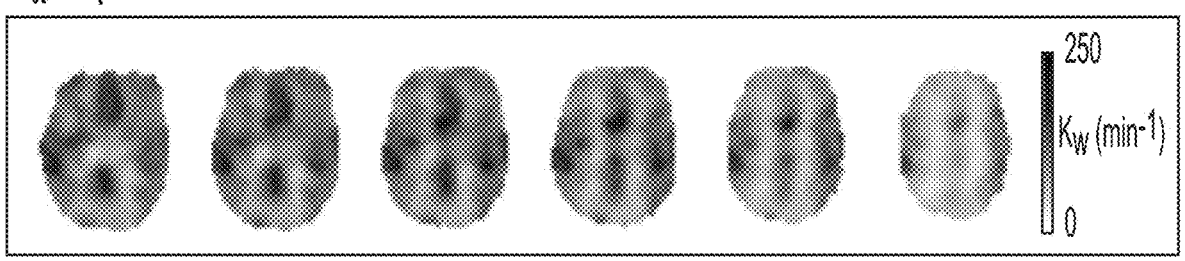

FIGS. 7A and B shows six slices of $k_w$ maps from test-retest scans ($k_w$=96.7 and 88.7 min⁻¹) of one representative subject (F, age=72 yrs).

Figure 8B:
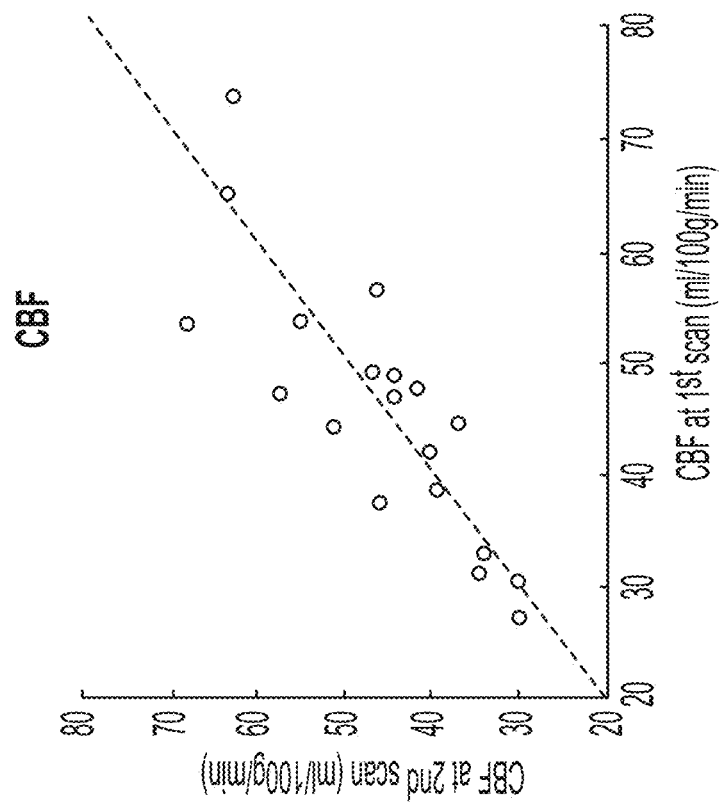
FIGS. 8A and 8B are graphs illustrating average $k_w$ and CBF measurements from test and retest experiments using a 3 dimensional (3D)-pCASL sequence according to an embodiment of the present disclosure.
Figure 8A:
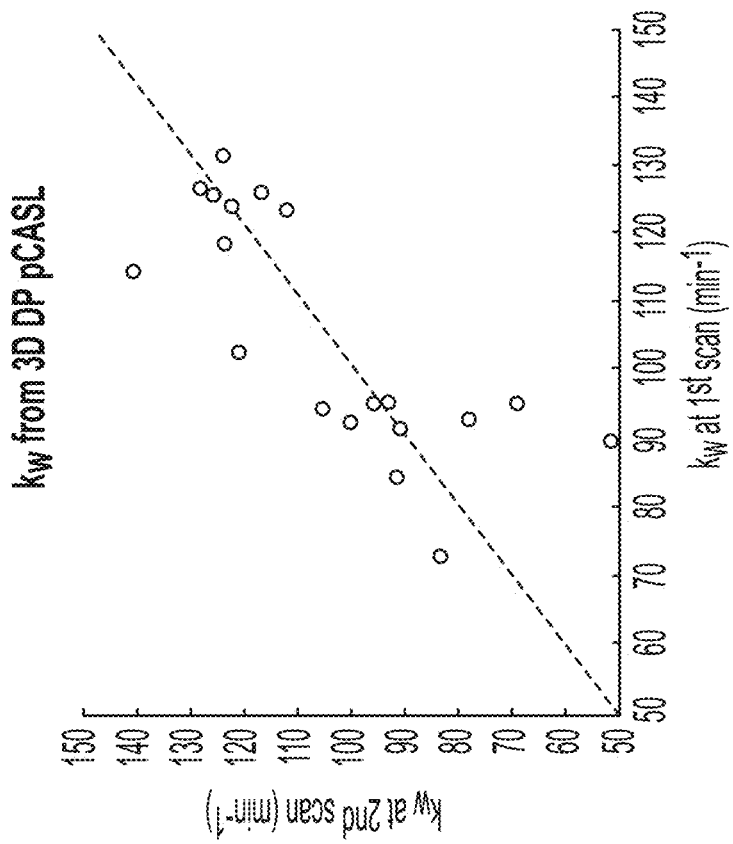

FIGS. 8A and 8B illustrate average $k_w$ and CBF values acquired at the second scan plotted against the $k_w$ and CBF values acquired at the re-scan.

A good test-retest reproducibility (ICC=0.75) was achieved for the proposed DP 3D GRASE pCASL sequence, whereas poor reproducibility was observed for 2D DW pCASL results (ICC=0.21). Table 1 below summarizes the average $k_w$ and ICC values of test and retest measurements from 19 subjects in the 8 ROIs. ICC ranges from 0.17 in parahippocampal gyrus and 0.3 in hippocampus to 0.63 in precuneus and 0.72 in frontal lobe, with an average of 0.52.

TABLE 1

Average $K_w$ and ICC values of test and restest measurements in 8 ROIs related to AD

|  | Average $K_w$ (min⁻¹) | ICC |
| --- | --- | --- |
| Frontal | 98.3 ± 20.8 | 0.72 |
| Temporal | 97.8 ± 17.3 | 0.54 |
| Parietal | 100.6 ± 22.2 | 0.52 |
| Hippocampus | 101.7 ± 22.4 | 0.30 |
| Para hippocampus gyrus | 88.9 ± 21.8 | 0.17 |
| Anterior cingulum | 106.6 ± 21.9 | 0.74 |
| Posterior cingulum | 108.6 ± 22.5 | 0.57 |
| Precuneus | 102.4 ± 19.9 | 0.63 |

Estimated average $k_w$ was 105.0±20.6, 109.6±18.9, and 94.1±19.6 min−1 for the whole brain, GM, and WM, respectively, which corresponds well with the literature. Average ATT was 1242.1±111.1, 1220.6±100.2, and 1288.8±113.7 ms for the whole brain, GM, and WM, respectively.

Average global CBF=45.6±11.6 mL/100 g/min across 19 aged subjects from both test and retest scans. CBF values of the whole brain acquired at the second scan are plotted against the CBF values acquired at the first scan. ICC=0.85 for CBF acquired from test and retest scans. No significant correlation was found between $k_w$ and CBF (β=0.35; P=0.22).

FIGS. 9A-9C illustrate scatter plot of hga1c (9A), Flanker (9B), PSMT (9C) versus $k_w$. Linear regression was indicated by the black dashed lines. FIGS. 9D-9F illustrate bar plot of $k_w$ in subject with diabetes and normal subjects (9D), and in subject groups with different $CDR_{SOB}$ (9E) and $CDR_{global}$ (9F) scores. In a cohort of aged subjects at risk of cerebral small vessel disease, a significant positive correlation was found between $k_w$ (whole brain/GM/WM) and HgA1c score, as shown in FIG. 9A, which indicates higher risk of diabetes is associated with increased BBB water exchange. Average whole brain $k_w$ in subjects with type 2 diabetes was 115.2±7.2 min⁻¹, which was 18.1% higher than average $k_w$ in normal subjects (97.5±12.9 min⁻¹), as shown in FIG. 9D. A significant positive correlation was found between $k_w$ (whole brain/GM/WM) and Cholesterol. Increased CDR_SOB/CDR_global scores and decreased Flanker/Picture Sequence Memory Test (PSMT) were significantly correlated with increased $k_w$, as shown in FIGS. 9B, 9C, 9E, and 9F, which indicates cognitive impairment is significantly associated with increased BBB water exchange rate. These results suggest that the method of FIG. 2 provides reliable measurement of water exchange rate $k_w$ that is able to detect subtle changes in BBB function associated with cerebral small vessel diseases.

FIG. 12 is a table 1200 summarizing the results of mixed-effects model analysis of $k_w$ (whole brain/GM/WM) using clinical and behavioral assessments as the independent variables, age and sex as covariates, and time (test-retest) as the random variable. Significant correlations with P values smaller than 0.05 and 0.005 are indicated by asterisks in the table 1200. No significant correlations between $k_w$ and age/sex were found in this study. Increased $k_w$ was found in subjects with type 2 diabetes (β=25.7; P<0.001) and hypercholesterolemia (β=17.8; P=0.04), which is consistent with DCE-MRI and biochemical studies. Increased $k_w$ was found in subjects with higher vascular risk factors (β=9.4; P=0.02). Both the global (CDR-GS, β=44.6; P=0.002) and sum of box scores (CDR-SB, β=21.0; P=0.001) of the Clinical Dementia Rating (CDR) scale were significant predictors of $k_w$, which indicates that increased BBB water exchange rate is associated with a greater severity of functional impairment. NIH toolbox measurements: Dimensional Change Card Sort (DCCS; β=−1.10; P=0.02), Picture Sequence Memory Test (PSMT)a (β=−0.98; P=0.03), and PSMTb (β=−1.19; P=0.001) were significantly correlated with $k_w$, and a trend of negative correlation was found between Flanker (β=−0.58; P=0.08) and $k_w$, which indicates that increased BBB water exchange rate is associated with a lower level of cognitive flexibility, worse episodic memory, and a trend of decreased attention/inhibitory control. $k_w$ was also significantly correlated with the Fazekas scale of WMH (β=10.61; P=0.04), which indicates that $k_w$ is associated with severity of WMH. A positive correlation between $k_w$ and WMH volume was also observed in this study, but failed to reach significance (β=1.68; P=0.20).

Additional experiments were performed on various test subjects to verify the method of FIG. 2. All subjects underwent MRI scans on a Siemens 3T Prisma system (available from Siemens of Erlangen, Germany) using a 20-channel head coil after they provided informed consent according to a protocol approved by the Institutional Review Board of the University of Southern California (Los Angeles, CA). A total of 28 subjects participated in the study, including 4 healthy volunteers (3 male; age=34±11 years) for pulse sequence optimization, 19 aged subjects (7 male; age=68.8±7.6 years, all Latinos) enrolled from the MarkVCID study (www.markvcid.org) for clinical evaluation of the developed pulse sequences, and 5 subjects from the same cohort (2 male; age=68±6 years) for comparison with 2D DW pCASL. Imaging parameters for the DP GRASE pCASL sequence were: field of view (FOV)=224 mm, matrix size=64×64, 12 slices (10% oversampling), resolution=3.5×3.5×8 mm3, turbo factor=14, EPI factor=64, bandwidth=3125 Hz/pixel, TE=36.5 ms, TR=4000 ms, label/control duration=1500 ms, centric ordering, timing of background suppression pulses was optimized to suppress gray matter (GM) and white matter (WM) signal, and duration of 4 diffusion gradient lobes=3.4/5.1/5.5/3.0 ms.

To determine the optimal bDW, the proposed sequence was performed in 4 healthy subjects with 3 PLDs (1500, 1800, and 2100 ms) and 6 b-values (b=0, 10, 25, 50, 100, and 200 s/mm2). Twenty repetitions (2 minutes 40 seconds) were acquired for each b-value. Biexponential fitting of ASL signals with 6 diffusion weightings was conducted to calculate the diffusion coefficients for capillary (Dc) and tissue (Db) compartments and determine the appropriate bDW that suppresses capillary signal with minimal effect on tissue signal (shown in Equation 15 below):

$$\frac{\Delta M_b}{\Delta M_0} = A_1 \cdot e^{-b \cdot D_c} + (1 - A_1) \cdot e^{-b \cdot D_b} \quad \text{Equation 15}$$

The experiments utilized a 2-stage approach known in the art to measure ATT and $k_w$. Fifteen repetitions were acquired for each b-value of the FEAST scan at PLD=900 ms with a total acquisition time of 4 minutes. $k_w$ was calculated from scans acquired at PLD=1800 ms, when the labeled blood reaches the microvascular compartment, with b=0 and $b_{DW}$. Twenty repetitions were acquired for each b-value of the $k_w$ scan, and total acquisition time was 6 minutes. An extra reference image without background suppression was acquired at the PLD of 2000 ms to generate CBF and the R1b map. CBF was calculated from the reference image and perfusion signal acquired at 1800 ms without diffusion weighting, using blood-tissue water partition coefficient=0.9 g/ml and labeling efficiency=77%.

MRI scans were performed in a cohort of elderly subjects enrolled in the MarkVCID study. Nineteen subjects were recruited and underwent 2 MRIs approximately 2 weeks apart to evaluate the reproducibility of the proposed sequence. Test-retest MRI scans were conducted on similar times of day to minimize potential effects of circadian rhythms, and subjects were abstinent from caffeine intake for at least 3 hours before MRI scans. For comparison, 2D DW pCASL scans were performed in 5 subjects from the same cohort. Imaging parameters of the 2D DW pCASL were: FOV=224 mm, matrix size=64×64, ⅞ partial Fourier factor, 12 slices, ascending ordering, slice gap=1 mm, resolution=3.5×3.5×8 mm³, bandwidth=3125 Hz/pixel, TE=48 ms, TR=4300 ms, label/control duration=1500 ms. Fifteen pairs were acquired at PLD=900 ms with b=0 and 10 (VENC=7.5 mm/s) s/mm², and 20 pairs were acquired at PLD=1800 ms with b=0 and 50 s/mm², respectively.

Subjects underwent a physical exam, medical history evaluation (hypertension, diabetes, and hypercholesterolemia), and blood draw before the first MRI scan. Presence or absence of hypertension, diabetes, and hypercholesterolemia was defined by a past diagnosis and/or current treatment for these conditions. Vascular risk factor (0-3) was calculated as the combination of presences of hypertension, diabetes, or hypercholesterolemia. Neuropsychological assessment was performed using the Alzheimer's Disease Centers' Uniform Data Set v3 (UDS3) as well as the NIH toolbox. Volumes of white matter hyperintensity (WMH) was manually segmented by a clinical fellow from T2-weighted fluid-attenuated inversion recovery (FLAIR) images (resolution=1×1×1 mm³, inversion time/TE/TR=1800/388/5000 ms) using ITK-SNAP (www.itksnap.org). The Fazekas scale of WMH was rated for each subject. Clinical information and descriptions of all clinical assessments are summarized in a table 1000 shown in FIG. 10.

Control/label images were corrected for rigid head motion offline using SPM12 (Wellcome Trust Centre for Neuroimaging, UCL, London, UK) and subtracted to obtain perfusion images. Temporal fluctuations in the difference image series owing to residual motion and physiological noise were minimized using an algorithm based on principal component analysis. $k_w$ and ATT maps were generated with a TGV regularized SPA model using average DW pCASL signals acquired at the PLDs of 900 and 1800 ms, as well as the R1b map generated from background suppressed control images in each individual subject. The alternating direction method of multipliers (ADMM; http://web.stanford.edu/—boyd/papers/admm_distr_stats.html) algorithm was implemented in Matlab (available from The MathWorks, Inc. of Natick, MA) to solve Equations (7) and (8).

Average $k_w$ and ATT were measured for the whole brain, GM, and WM, respectively. GM and WM masks were segmented using SPM12 based on coregistered 3D magnetization-prepared rapid gradient echo (MP-RAGE) images. The test-retest reproducibility of average $k_w$ and CBF in the whole brain was quantified by intraclass correlation coefficient (ICC). The $k_w$ maps were then normalized into the canonical Montreal Neurological Institute space, and the ICC of $k_w$ was also computed in 8 regions of interests (ROIs) related to AD: frontal lobe, temporal lobe, parietal lobe, hippocampus, parahippocampal gyrus, anterior/posterior cingulum, and precuneus. Correlation between average $k_w$ from both test and retest scans and clinical/behavioral assessments were evaluated using a mixed-effects linear regression model implemented in STATA software (version 13.1; available from StataCorp LP of College Station, TX), incorporating age and sex as co-variates and time (test/retest) as the random variable. Mixed-effects linear regression was also performed to evaluate the correlation between average $k_w$ and CBF from test and retest scans. Two significant levels were set as P value less than 0.05 and 0.005 (2-sided).

Figure 11:
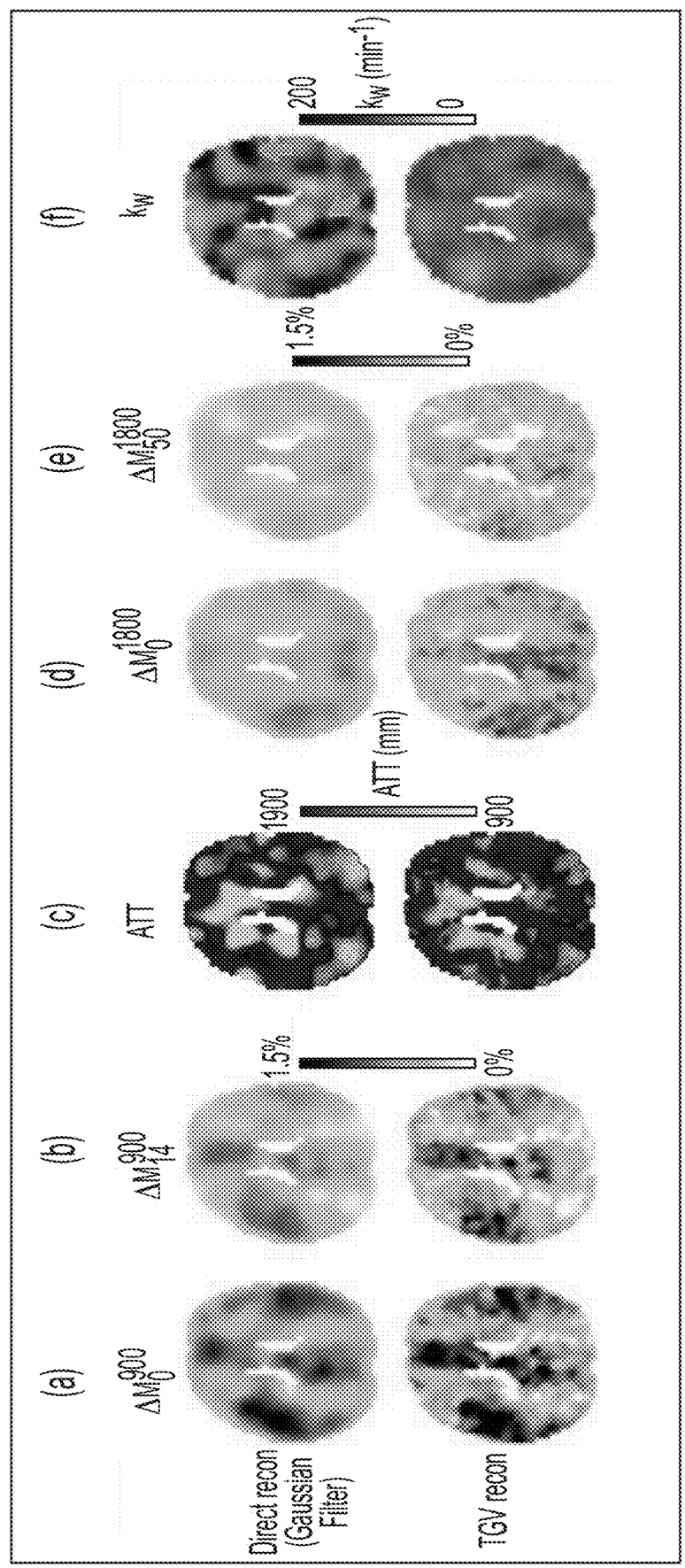
FIG. 11 is a scan illustrating a comparison of direct modeling with Gaussian smoothing and TGV regularized SPA modeling according to an embodiment of the present disclosure.

FIG. 11 shows a comparison results from direct SPA modeling with a Gaussian filter (first row) and the proposed SPA modeling with TGV regularization (second row). (a) and (b) show the perfusion maps acquired at the PLD of 900 ms without and with diffusion weighting for vascular signal suppression (b=14 s/mm²), respectively. (d) and (e) show the perfusion maps acquired at PLD of 1800 ms without and with diffusion weighting for suppression of the microvascular/capillary the signal (b=50 s/mm²). A 3D Gaussian filter with a full-width at half maximum (FWHM) of 5 mm was applied to obtain the perfusion images in the first row of (a), (b), (d), and (e). (c) shows estimated ATT maps. Prolonged ATT is observed in the posterior area, which is consistent with previous findings. (f) shows the $k_w$ map estimated from direct SPA modeling (first row) and the proposed TGV regularized SPA modeling (second row). Direct SPA modeling with a Gaussian filter generates smoother $k_w$ maps whereas TGV regularized SPA modeling preserved the original image resolution. The local bright regions (indicated by red arrows, $k_w$>200 min$^{-1}$) with spuriously high $k_w$ values in direct SPA modeling were suppressed by TGV regularized SPA modeling.

The present disclosure proposed a new MR pulse sequence for DW pCASL with improved test-retest repeatability by integrating a diffusion preparation module optimized for minimizing eddy current and spoiling of non-CPMG signals with background suppressed 3D GRASE pCASL to quantify the water exchange rate ($k_w$) across the BBB. Given that water molecules are much smaller than the GBCAs and transcapillary water exchange is mainly through aquaporin, assessing $k_w$ could potentially provide a more direct and sensitive assessment of BBB dysfunction at an earlier stage of disease progression compared to conventional contrast-enhanced MRI. The proposed technique is capable of generating whole-brain ATT and a $k_w$ map within 10 minutes, which is comparable to or shorter than clinical DCE-MRI protocols. Without any radiation or contrast injection, the proposed technique is suitable for repeated scans for longitudinal studies or populations not suitable for DCE-MRI (e.g., children and subjects with renal dysfunction). ICC of the test and retest scans of the proposed DP 3D GRASE pCASL sequence is 0.75 for the whole brain across repeated scans 2 weeks apart, which is comparable to or slightly lower than reported test-retest reproducibility of ASL CBF measurements. Fair to good reproducibility (ICC, ~0.50-0.75) of $k_w$ in ROIs was also observed, except for smaller regions such as the hippocampus and parahippocampal gyrus. These data suggest that $k_w$ may provide a reliable biomarker of BBB function to track disease progression and treatment effects in a clinical trial on SVD and/or dementia.

3D GRASE was recommended by an ASL white paper for clinical implementations of pCASL perfusion MRI. However, it has been challenging to combine diffusion weightings with 3D turbo-spin echo (TSE)-based sequences. Diffusion gradients induce extra phase attributed to bulk motion (e.g., head movement or respiration). Violation of the CPMG condition causes rapid signal decrease in regions where induced phase is not along Meiboom-Gill (MG) phase direction, leading to dark bands or shades in images. Ensuring the refocusing pulse to be exactly 180° is the most straightforward approach to avoid phase sensitivity, which is not commonly used because of specific absorption rate limitations, and a small deviation from 180° is sufficient to introduce artifacts. Motion-compensated diffusion preparation has been proposed to reduce the sensitivity of TSE to bulk motion. However, it is not suitable for the FEAST scheme to measure ATT given that vascular signal is compensated. Other methods, including echo splitting, which doubles the echo spacing, or quadratic phase modulation of refocusing phases, which requires long echo train, have been proposed. However, these methods are not suitable for this study because long GRASE readout causes image blurring attributed to T2 relaxation. The non-CPMG diffusion preparation adopted in this study has been proven to be robust to motion, however, at the cost of half signal loss. The present study utilized a relatively thick slice (8 mm) to compensate for SNR loss.

Another innovation of the present disclosure is TGV regularized SPA modeling. In the original SPA modeling strategy, the estimated $k_w$ is very sensitive to noise when the tissue fraction is close to 1. This challenge is accentuated by the relatively low SNR of ASL signals. Including spatial regularization in the SPA modeling would improve the reliability of $k_w$ estimation, which typically utilizes the TV metric. The TGV is an improved mathematical framework based on minimizing both first-order and second-order TV to avoid blotchy appearances commonly observed in TV-constrained image reconstruction, which has also been applied for ASL denoising. In the present disclosure, preservation of the original image resolution was enabled, minimizing spuriously high $k_w$ values while improving SNR using TGV regularized SPA modeling. Sensitivity analysis of $k_w$ versus weighting factor λ, was performed by calculating $k_w$ in a representative subject with λ varying from 0.01 to 0.10 at a step size of 0.01, around ±5% changes of $k_w$ was observed as compared to the $k_w$ calculated with λ=0.05. Using the ADMM algorithm, the average calculation time was within 1 minute on a stand-alone computer (2.3-GHz dual-core processor).

There is growing evidence indicating that BBB permeability increases with age, and these changes are accelerated in microvascular disease and dementia. Loss of BBB integrity may contribute to progression of SVD by allowing neurotoxin access to the brain and causing ionic imbalance, an inflammatory response around vessels, and eventually demyelination of WM fibers. Elevated levels of albumin, which does not cross the intact BBB, in cerebrospinal fluid (CSF) has been reported in patients with vascular dementia. BBB dysfunction has also been implicated in the pathogenesis of AD. Currently, assessment of BBB permeability relies on CSF sampling and/or DCE-MRI using GBCAs. Biochemical assays of CSF require lumbar puncture whereas DCE-MRI requires administration of contrast and long scan time (>15 minutes). In addition, because albumin (66 kDa) and contrast agents (550 Da) have relatively large molecular weights, BBB permeability has to reach a critical level before extravasation occurs.

The present disclosure discovered significantly increased $k_w$ in subjects with type 2 diabetes and hypercholesterolemia, both of which have emerged as risk factors for SVD and AD. Hypercholesterolemia has been known to be associated with vascular pathology and dysfunction, including vascular inflammation and atherosclerosis, which may lead to early breakdown of the BBB. Diabetes mellitus leads to glycosylation of endothelial proteins and also causes the basement membrane in the vessel wall to grow abnormally thicker and weaker. As a result, the microvessels in the brain and body of diabetic subjects are susceptible to microbleeds, protein leakage, and hypoperfusion. Population-based studies have shown that both diabetes and hypercholesterolemia lead to increased risk of neurodegeneration, cognitive impairment, and dementia. The present observation of increased $k_w$ in subjects with diabetes and hypercholesterolemia and total vascular risk factors is consistent with existing literature, suggesting that $k_w$ may provide a surrogate imaging biomarker of cerebral effects of common vascular risk factors and early SVD and/or AD.

It was also observed that increased $k_w$ in subjects with decreased neurocognitive performance, including increased CDR-SB/CDR-GS scores and decreased Flanker/DCCS/PSMT. Both CDR-SB and CDR-GS have been widely used in staging dementia severity. The Flanker, DCCS, and PSMT are tests of attention/inhibitory control, cognitive flexibility, and episodic memory, respectively. Increased $k_w$ was also associated with increased Fazekas scale and showed a trend of positive correlation with WMH volume. A pathological report has associated WMH with demyelination and axonal loss, and clinical studies have shown associations between WMH and progressive cognitive impairment and increased risk of dementia. Although previous studies reported globally reduced CBF in cerebral SVD patients with greater WMHs, the $k_w$ changes in 19 subjects with potential SVD were not significantly associated with CBF changes in this study. Subjects recruited in this study are in the early stages of WMH development (average WMH volume is 2.6 cm3), and its association with $k_w$ will provide important opportunities to prevent brain damage attributed to SVD at the earliest stages and ameliorate cognitive impairment.

Recently, global water extraction fraction (Ew) and PSw were determined by measuring arterially labeled blood spins that are drained into cerebral veins, which generates reliable results in several minutes but cannot reveal BBB water exchange change in local regions. Kinetic models were proposed to map the whole-brain transcapillary water exchange based on the T2 and T2* differences in the 2 compartments. However, reliable and accurate quantification remains challenging because of the small differences of T2/T2*. A new method for estimating water permeability (PSw) was proposed recently by utilizing the intrinsic diffusion weighting of GRASE read-out, but requires sophisticated deconvolution algorithms. In this study, the b-value of a pair of crusher gradients in a GRASE readout was 0.04, 0.09, and 0.02 s/mm2 along x, y, and z directions, respectively. The blurring effects along partition direction caused by the intrinsic diffusion weighting of the GRASE readout was negligible with the FWHM of the point spread function smaller than 1.03/1.003 voxel size for the capillary/tissue signal. The strength of the technique is that there are 2 orders of magnitude difference between the (pseudo-)diffusion coefficients of the intravascular and extravascular spaces, which can be separated by a small diffusion gradient. Although a slight variation of the diffusion coefficient (Dc/Db) was observed at 3 PLDs, which is consistent with a previous study, the differentiation between capillary and tissue space is reliable given the large diffusion coefficient difference (~100-fold). The sensitivity analysis showed that a ±20% change in bDW only induces ~±1% change in remaining capillary signal.

Alternative arterial spin labeling methods such as pulsed ASL (PASL) and velocity-selective ASL (VS-ASL), as well as alternative 3D acquisitions such as turbo spin-echo (TSE) and echo planar imaging (EPI) may be applied for mapping BBB water exchange.

Possible limitations of this study may exist. Because segmented acquisition introduces intersegment phase inconsistency and shading artifacts, single-shot acquisition may be required for the proposed DP 3D pCASL sequence. Resolution of the $k_w$/ATT map is relatively low as compared to standard ASL studies (also to compensate for half signal loss). To improve spatial resolution, fast imaging, such as 2D controlled aliasing in volumetric parallel imaging, and reconstruction algorithm with spatial and temporal constraints will be utilized. For comparison of 2D and 3D $k_w$ measurements, the sample size of the 2D experiment was small. Presence of arterial and venous compartments, which were considered as nonexchangeable compartments, may bias the capillary/tissue fraction estimation. The PLD of 1800 ms was chosen to exclude/minimize the arterial and venous compartments, because ATT was estimated to be 1200 to 1300 ms in this study, and it has been reported that detectable venous signals may exist at PLD>2500 ms. Recent studies also reported water exchange in periarterial and perivenous spaces through aquaporin. This study has demonstrated the potential of $k_w$ as a sensitive marker of BBB water exchange. However, Vc may alter in diseases (e.g., decreased Vc in diabetes attributed to thicken vessel wall and increased perivascular space) and complicates the understanding of the relation between $k_w$ and PSw. With the proposed sequence, total extraction ratio Ew and PSw can be computed with DP 3D pCASL signals acquired at longer PLD (>2.5 seconds), which remains to be explored in future studies.

A DP 3D GRASE pCASL sequence with TGV regularized SPA modeling was proposed to measure BBB water exchange noninvasively with good reproducibility in a cohort of aged subjects at risk of SVD. This study demonstrated the capability of $k_w$ being a surrogate imaging biomarker for SVD and early dementia. Its clinical use for detection of BBB dysfunction before leakage of large-molecule contrast agents awaits further evaluation.

Exemplary embodiments of the methods/systems have been disclosed in an illustrative style. Accordingly, the terminology employed throughout should be read in a non-limiting manner. Although minor modifications to the teachings herein will occur to those well versed in the art, it shall be understood that what is intended to be circumscribed within the scope of the patent warranted hereon are all such embodiments that reasonably fall within the scope of the advancement to the art hereby contributed, and that that scope shall not be restricted, except in light of the appended claims and their equivalents.

What is claimed is:

1. A method for measuring water exchange across a blood-brain barrier based on diffusion weighted (DW) arterial spin labeling (ASL) magnetic resonance imaging (MRI) signals comprising:
   acquiring a plurality of diffusion weighted (DW) arterial spin labeling (ASL) magnetic resonance imaging (MRI) signals;
   determining optimal parameters to separate labeled water in capillary and brain tissue compartments; and
   estimating a water exchange rate across the blood-brain barrier based on the plurality of DW ASL MRI signals and the optimal parameters, using a total generalized variation (TGV) regularized single-pass approximation (SPA) modeling algorithm wherein the TGV is an enhanced framework for estimating a given arterial transit time (ATT) and the water exchange rate based on minimizing both first-order and second-order total variation (TV) for denoising the plurality of DW ASL MRI signals.

2. The method of claim 1 wherein:
   the acquiring the plurality of DW ASL MRI signals further comprises acquisition of a set of DW ASL MRI signals using a diffusion prepared three-dimensional (3D) gradient and spin echo (GRASE) and a background suppressed pseudo continuous arterial spin labeling (pCASL), and
   a diffusion preparation was implemented before the diffusion prepared 3D GRASE.

3. The method of claim 1 wherein acquiring the DW ASL MRI signals includes formulating diffusion gradients in bipolar pairs along at least one of slice direction or other directions and optimizing timing to minimize eddy current.

4. The method of claim 3 wherein acquiring the DW ASL MRI signals further includes applying an additional dephasing gradient along a phase-encoding (PE) direction after the formulating diffusion gradients in bipolar pairs to induce a linear phase increment along the PE direction to dephase a non-Carr-Purcell-Meiboom-Gill (CPMG) signal that is affected by phase errors caused by bulk motion during a diffusion encoding.

5. The method of claim 4 further comprising adding a pair of re-phasing and rewound dephasing gradients before and after each refocusing pulse to maintain CPMG condition and to balance a gradient moment.

6. The method of claim 4 further comprising 3D turbo spin echo readout in conjunction with a de-phasing gradient after bi-polar gradients during diffusion preparation.

7. The method of claim 1 wherein determining the optimal parameters includes selecting at least one of optimal b values or optimal diffusion weighting values.

8. The method of claim 7 wherein selecting the at least one of the optimal b values or the optimal diffusion weighting values includes determining appropriate parameters which suppress capillary signals with minimal effects on tissue signals.

9. The method of claim 1 further comprising estimating arterial transit time based on the DW ASL MRI signals and the optimal parameters.

10. A method for measuring water exchange across a blood-brain barrier comprising:
 acquiring a plurality of diffusion weighted (DW) arterial spin labeling (ASL) magnetic resonance imaging (MRI) signals using a diffusion prepared three-dimensional (3D) gradient and spin echo (GRASE) and background suppressed pseudo-continuous arterial spin labeling (pCASL);
 determining optimal parameters to separate labeled water in capillary and brain tissue compartments including selecting at least one of optimal b values or optimal diffusion weighting values; and
 estimating a water exchange rate across the blood-brain barrier based on the plurality of DW ASL MRI signals and the optimal parameters, using a total generalized variation (TGV) regularized single-pass approximation (SPA) modeling algorithm wherein the TGV is an enhanced framework for estimating a given arterial transit time (ATT) and the water exchange rate ($k_w$) based on minimizing both first-order and second-order total variation (TV) for denoising the plurality of DW ASL MRI signals.

11. The method of claim 10 wherein a diffusion preparation was implemented before the 3D GRASE.

12. The method of claim 10 wherein acquiring the DW ASL MRI signals includes formulating diffusion gradients in bipolar pairs along at least one of slice direction or other directions and optimizing timing to minimize eddy current.

13. The method of claim 12 wherein acquiring the DW ASL MRI signals further includes applying an additional de-phasing gradient along a phase-encoding (PE) direction after the formulating diffusion gradients in bipolar pairs to induce a linear phase increment along the PE direction to dephase a non-Carr-Purcell-Meiboom-Gill (CPMG) signal that is affected by phase errors caused by bulk motion during a diffusion encoding.

14. The method of claim 12 further comprising adding a pair of re-phasing and rewound dephasing gradients before and after each refocusing pulse to maintain CPMG condition and to balance a gradient moment.

15. The method of claim 12 further comprising alternating a phase of refocusing pulses of 3D gradient and spin echo readout to minimize non-CPMG artifacts without applying a de-phasing gradient after bi-polar gradients during diffusion preparation.

16. The method of claim 10 wherein selecting the at least one of the optimal b values or the optimal diffusion weighting values includes determining appropriate parameters which suppress capillary signals with minimal effects on tissue signals.

17. A method for measuring water exchange across a blood-brain barrier comprising:
 acquiring a plurality of diffusion weighted (DW) arterial spin labeling (ASL) magnetic resonance imaging (MRI) signals using a diffusion prepared three-dimensional (3D) gradient and spin echo (GRASE) and background suppressed pseudo-continuous arterial spin labeling (pCASL), and by formulating diffusion gradients in bipolar pairs along at least one of slice direction or other directions and optimizing timing to minimize eddy current;
 determining optimal parameters to separate labeled water in capillary and brain tissue compartments including selecting at least one of optimal b values or optimal diffusion weighting values; and
 estimating a water exchange rate across the blood-brain barrier based on the DW ASL MRI signals and the optimal parameters, using a total generalized variation (TGV) regularized single-pass approximation (SPA) modeling algorithm wherein the TGV is an enhanced framework for estimating a given arterial transit time (ATT) and the water exchange rate ($k_w$) based on minimizing both first-order and second-order total variation (TV) for denoising the plurality of DW ASL MRI signals.

18. The method of claim 10 wherein the water exchange rate ($k_w$) comprises a capillary permeability surface-area product of water ($PS_w$) divided by a distribution volume of water tracer in a capillary space ($V_c$) that is calculated based on a monotonic relationship with a fraction of a capillary signal at the given arterial transit time (ATT).

* * * * *